United States Patent
Fisher

(10) Patent No.: US 6,881,061 B2
(45) Date of Patent: Apr. 19, 2005

(54) ULTRASONIC METHOD FOR CLEANING TEETH

(75) Inventor: Adarrel Omar Fisher, Bensalem, PA (US)

(73) Assignee: McNeil-PPC, Inc., Skillman, NJ (US)

(*) Notice: Subject to any disclaimer, the term of this patent is extended or adjusted under 35 U.S.C. 154(b) by 44 days.

(21) Appl. No.: 10/261,347

(22) Filed: Sep. 30, 2002

(65) Prior Publication Data

US 2004/0063074 A1 Apr. 1, 2004

(51) Int. Cl.[7] ............................................. A61C 15/00
(52) U.S. Cl. ........................................ 433/216; 433/119
(58) Field of Search .................................. 433/119, 216, 433/118; 601/162, 163, 164; 606/169, 170, 171

(56) References Cited

U.S. PATENT DOCUMENTS

| | | | | |
|---|---|---|---|---|
| 3,380,446 A | * | 4/1968 | Martin | 601/2 |
| 3,401,690 A | * | 9/1968 | Martin | 604/22 |
| 3,522,801 A | * | 8/1970 | Robinson | 433/86 |
| 3,547,110 A | * | 12/1970 | Balamuth | 601/162 |
| 3,636,947 A | * | 1/1972 | Balamuth | 601/162 |
| 3,828,770 A | * | 8/1974 | Kuris et al. | 601/142 |
| 4,961,923 A | * | 10/1990 | Heyde | 424/49 |
| 5,013,241 A | * | 5/1991 | von Gutfeld et al. | 433/86 |
| 5,451,161 A | * | 9/1995 | Sharp | 433/119 |
| 5,730,594 A | * | 3/1998 | Sharp | 433/119 |
| 6,313,565 B1 | | 11/2001 | Puskas | |

* cited by examiner

Primary Examiner—Cary E. O'Connor

(57) ABSTRACT

An improved method for cleaning teeth is disclosed. The method for cleaning teeth includes: applying ultrasonic waves of a first frequency through a liquid media to the teeth for a first period of time; and applying ultrasonic waves of a second frequency through a liquid media to the teeth for a second period of time.

8 Claims, No Drawings

ULTRASONIC METHOD FOR CLEANING TEETH

BACKGROUND OF THE INVENTION

1. Field of the Invention

This invention relates to a method for cleaning teeth that utilizes an ultrasonic system. The ultrasonic cleaning method of the present invention comprises the application through a suitable medium of ultrasonic waves at a first frequency for a first period of time, followed by the application through the medium of ultrasonic waves at a second frequency for a second period time. The ultrasonic waves are preferably transmitted through a liquid medium which contacts the teeth. The ultrasonic waves form bubbles in the medium. The break up or disintegrate bubbles on contact with the teeth. This results in improved cleaning of the teeth.

2. Description of the Prior Art

For many years, manual toothbrushes were the predominant means for cleaning teeth. Manual toothbrushes typically have a plastic handle attached to a plastic head. Plastic bristles for cleaning the teeth are attached to the head. The motion required for cleaning the teeth is manually provided by the consumer.

While manual toothbrushes are effective to clean teeth, especially when combined with flossing, many consumers feel that the equipment and methods used in their dentist's office to clean their teeth are much more effective. Recently, many consumers have converted to using power toothbrushes.

Power toothbrushes are typically energized by a battery. The battery powers a motor having an output shaft which typically rotates or reciprocates. The rotation or reciprocation of the output shaft ultimately is converted into motion in the brush head of the toothbrush. Power toothbrushes with brush heads that reciprocate, rotate, and/or oscillate are all known in the art. While the power toothbrushes are seen as more effective at cleaning the teeth than manual toothbrushes, they are still not viewed as equal to the dentist's office cleaning equipment and methods.

Power toothbrushes with ultrasonic cleaning have recently been introduced to the market. These ultrasonic toothbrushes have a transducer that operates at a single frequency. Ultrasonic waves are transmitted from the toothbrush through a suitable medium to the teeth and gums. These ultrasonic toothbrushes are generally viewed as better at cleaning the teeth than conventional power toothbrushes, but still do not provide the same effective cleaning as the dentist's office equipment and methods.

U.S. Pat. No. 6,313,565 teaches a cleaning system that utilizes different frequency ultrasonic waves simultaneously applied to improve cleaning. The ultrasonic waves are generated by multiple transducers and may be at a frequency ranging from 9 kilohertz (kHz) to 5 megahertz (MHz).

Despite the disclosure of the above-mentioned reference, there is a continuing need for a tooth cleaning system that is more effective at cleaning the teeth.

SUMMARY OF THE INVENTION

We have surprisingly found that a tooth cleaning system that utilizes at least two different ultrasonic wave frequencies intermittently or consecutively applied provides improved tooth cleaning.

In one embodiment, the present invention provides a method for cleaning teeth including: applying ultrasonic waves of a first frequency through a liquid medium to the teeth for a first period of time; and applying ultrasonic waves of a second frequency through a liquid medium to the teeth for a second period of time.

DETAILED DESCRIPTION OF PREFERRED EMBODIMENTS

The cleaning method of the present invention utilizes ultrasonic waves of a first frequency and ultrasonic waves of a second frequency. As is known in the art, ultrasonic waves are generated by power transducers. Transducers receive electrical energy and convert the energy to mechanical energy, which is then converted to ultrasonic energy. In the method of the present invention, electrical energy is converted to ultrasonic energy. The ultrasonic energy is generated at at least two different frequencies.

Various transducers are commercially available and can be designed to suit different applications. For example, ultrasonic baths are commercially available in different sizes and may operate at different frequencies.

In the method of the present invention, the first frequency may range from 20 kHz to 40 kHz, preferably 25 kHz to 40 kHz. The second frequency may range from 41 kHz to 70 kHz, preferably 41 kHz to 55 kHz.

The periods of time for which the different ultrasonic frequencies are applied will vary depending on the frequencies used, the temperature and pressure of the liquid medium, rectified diffusion threshold, and the desired degree of cleaning. Generally, the first frequency is applied to the teeth for from about 20 seconds to about two minutes, for example from about 30 seconds to about one minute. Generally, the second frequency is applied to the teeth for from about 20 seconds to about two minutes, for example from about 30 seconds to about one minute.

The first and second frequencies may be applied consecutively or intermittently. As used herein, "applied consecutively" means that a first frequency is applied, and then a second frequency is applied to complete a cleaning cycle. As used herein, "applied intermittently" means that first and second frequencies are alternately applied continuously, i.e., a number of times, throughout a cleaning cycle. The frequencies preferably are applied intermittently.

The ultrasonic waves are preferably applied to the teeth through a liquid medium. The liquid medium may be any liquid or gel suitable for oral care applications. Suitable liquid media include, but are not limited to, water, carbonated water, glycerin, toothpaste, and tooth cleaning gels. Preferably the liquid medium is capable of cavitation. The temperature of the liquid medium may range from about 20° C. to about 60° C., preferably from about 35° C. to about 45° C.

In practicing the cleaning method of the present invention, the liquid medium is brought into contact with the teeth to be cleaned. The liquid medium may be brought into contact with the teeth by means known in the art. For example, the liquid medium may be placed in a mouthpiece or tray designed to fit around teeth. Such a mouthpiece or tray is generally "U" shaped and may be molded to fit the user's teeth. Alternatively, the liquid medium may be continuously sprayed or pumped onto the surface of the teeth with commercially available equipment, such as a WATER PIK® Brand oral irrigation device.

As mentioned above, the liquid medium is preferably capable of cavitation, i.e., the medium is capable of having bubbles formed therein by virtue of ultrasonic energy being applied thereto. The size of the bubbles generated in the medium will vary depending on the frequency applied to the liquid medium and the particular liquid medium being utilized. While not wishing to be bound by theory, it is believed that different size bubbles affect the kind of cleaning of the method of the invention. For example, smaller bubbles may provide improved cleaning between the teeth, while larger bubbles may provide improved cleaning on the surface of the teeth.

Examples are provided below to further illustrate the method of the present invention. The invention should not be construed as being limited to the specific details set forth herein.

EXAMPLES

The method of the present invention was carried out utilizing the following apparatus and materials: an ultrasonic bath sold by Crest Ultrasonics, 0.5 Gallon, Model 175HT (38–40 kHz); an ultrasonic bath sold by Soniclean, 0.5 Gallon, Model 80T (41–44 kHz); extrinsically stained cow's teeth; a Colorimeter sold by Minolta, Model CR-321; a Hydrophone sold by Sensor/B.M. Hi-Tech Inc., Model SA-20; a Digital Oscilloscope sold by Link Instruments, Model DSO-2100; Emery 917 glycerin, 94.7% USP; and Kosher tap water.

Twenty-four (24) extrinsically stained cow's teeth were selected for the experiments described below. Initial L* (whiteness), a* (red-green color) and b* (yellow-blue color) color readings were taken on each of the twenty-four cow's teeth using the Minolta Colorimeter. The cow's teeth were divided into eight groups of three.

Two sets of experiments were conducted.

First Set of Experiments

For the first set of experiments, Kosher tap water was used as the liquid medium. Two ultrasonic baths were employed. A Soniclean Model 80T, operating at 41–44 kHz, was used as one bath. A Crest Ultrasonics Model 175HT, operating at 38–40 kHz, was used as the other bath.

Both operating frequencies were verified by using the Hydrophone connected to the Distal Oscilloscope. The Kosher tap water used in each ultrasonic bath was maintained at a temperature of approximately 40° C.

The first group of three cow's teeth was treated for two minutes in the aforementioned Soniclean ultrasonic bath operating at a frequency of 41–44 kHz.

The second group of three cow's teeth was treated for two minutes in the Crest Ultrasonics bath operating at 38–40 kHz.

The third group of three cow's teeth was first treated for one minute in the Crest Ultrasonics bath operating at 38–40 kHz and then for one minute in the Soniclean bath operating at 41–44 kHz.

The fourth group of three cow's teeth was first treated for one minute in the Soniclean bath operating at 41–44 kHz and then for one minute in the Crest Ultrasonics bath for one minute at 38–40 kHz.

After treatment as set forth above, the groups of cow's teeth were removed from the treatment bath, rinsed and set to dry in a laboratory hood for 30 minutes. The color of the teeth was then measured using the Minolta Colorimeter.

Second Set of Experiments

A second set of experiments was conducted using the remaining twelve cow's teeth. The experimental conditions were the same as those used for the First Set of Experiments except that glycerin, maintained at a temperature of approximately 53° C., was used as the liquid medium.

The overall change in the color, ΔE, of the treated teeth was calculated using the CIELAB equation $$\Delta E = [(\Delta L^*)^2 + (\Delta a^*)^2 + (\Delta b^*)^2]^{1/2}$$

where $\Delta L^*$, $\Delta a^*$ and $\Delta b^*$ represent the specific changes in whiteness, red-green color, and yellow-blue color, respectively, resulting from the specific cleaning procedure under consideration. The calculated ΔE value indicates the efficacy of the tested ultrasonic cleaning methods in removing stain and whitening teeth. Initial and post-cleaning L*, a*, and b* values were determined using the Minolta Colorimeter. The scores for each group of teeth were averaged. The scores are reported in Table 1.

TABLE 1

| | | Tooth Cleaning Scores, ΔE* Liquid Medium | |
|---|---|---|---|
| Frequency, kHz | Time, minutes | Kosher Tap Water | Glycerin |
| 38–40 | 2 | 1.53 | 1.56 |
| 41–44 | 2 | 1.18 | 2.9 |
| 38–40, then 41–44 | 1 1 | 2.79 | 3.9 |
| 41–44, then 38–40 | 1 1 | 2.19 | 3.76 |

*higher number = better cleaning

The data in Table 1 above demonstrate that the use of two ultrasonic frequencies applied consecutively cleans teeth better than either ultrasonic frequency alone. It also indicates that, under the above stated experimental conditions, glycerin is preferred over Kosher tap water as the liquid medium. The data also indicates that when water is used as the liquid medium, better cleaning is obtained when the teeth to be cleaned are initially treated with low frequency ultrasonic waves and are thereafter treated with higher frequency ultrasonic waves.

What is claimed:

1. A method for cleaning teeth comprising:
    applying ultrasonic waves of a first frequency through a liquid medium to teeth to be cleaned for a first period of time; and applying ultrasonic waves of a second frequency through a liquid medium to teeth to be cleaned for a second period of time.

2. The method of claim 1 wherein the ultrasonic waves of a first frequency and the ultrasonic waves of a second frequency are applied intermittently.

3. The method of claim 1 wherein the ultrasonic waves of a first frequency and the ultrasonic waves of a second frequency are applied consecutively.

4. The method of claim 1 wherein the first frequency ranges from about 20 kHz to about 40 kHz and the second frequency ranges from about 41 kHz to about 70 kHz.

5. The method of claim 4 wherein the first frequency ranges from about 25 kHz to about 40 kHz and the second frequency ranges from about 41 kHz to about 55 kHz.

6. The method of claim 1 wherein the liquid medium comprises water.

7. The method of claim 1 wherein the liquid medium is glycerin.

8. The method of claim 1 wherein low frequency ultrasonic waves are applied prior to the application of higher frequency ultrasonic waves.

* * * * *